United States Patent
Herger et al.

(10) Patent No.: US 10,847,263 B2
(45) Date of Patent: *Nov. 24, 2020

(54) HEAD MOUNTED VIDEO AND TOUCH DETECTION FOR HEALTHCARE FACILITY HYGIENE

(71) Applicant: INTERNATIONAL BUSINESS MACHINES CORPORATION, Armonk, NY (US)

(72) Inventors: Lorraine M. Herger, Port Chester, NY (US); Neal M. Keller, Pleasantville, NY (US); James R. Kozloski, New Fairfield, CT (US); Matthew McCarthy, Holly Springs, NC (US); Clifford A. Pickover, Yorktown Heights, NY (US); Andrew P. Wyskida, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 165 days.

This patent is subject to a terminal disclaimer.

(21) Appl. No.: 15/479,819

(22) Filed: Apr. 5, 2017

(65) Prior Publication Data
US 2017/0213079 A1   Jul. 27, 2017

Related U.S. Application Data

(63) Continuation of application No. 14/245,021, filed on Apr. 4, 2014, now Pat. No. 9,659,367.

(51) Int. Cl.
*G16H 40/20* (2018.01)
*G06T 7/00* (2017.01)
(Continued)

(52) U.S. Cl.
CPC .......... *G16H 40/20* (2018.01); *G06F 19/321* (2013.01); *G06K 9/00355* (2013.01);
(Continued)

(58) Field of Classification Search
CPC ....... G01C 11/04; G01S 17/89; G01S 7/4808; G06K 9/00476; G06K 9/00637;
(Continued)

(56) References Cited

U.S. PATENT DOCUMENTS 8,241,223 B2   8/2012   Gavriely et al.
2004/0138556 A1   7/2004   Cosman
(Continued)

FOREIGN PATENT DOCUMENTS

WO   WO2010034125 A1   4/2010

OTHER PUBLICATIONS

Meyers et al.; Network theory and SARS: Predicting outbreak diversity; Journal of Theoretical Biology 232 (2005), 71-81 (Year: 2005).*

(Continued)

*Primary Examiner* — Manuchehr Rahmjoo
(74) *Attorney, Agent, or Firm* — Tutunjian & Bitetto, P.C.; Rabin Bhattacharya

(57) ABSTRACT

A system and method tracks touches in a healthcare environment in order to analyze paths of transmission and contamination for the purpose of eliminating and containing transmission of colonizing, drug-resistant pathogens. Touches are identified and tracked with the use of recording devices. Each touch is logged and a touch graph is generated to identify transmission paths.

17 Claims, 7 Drawing Sheets

(51) Int. Cl.
*G06N 20/00* (2019.01)
*G06T 7/70* (2017.01)
*G16H 50/30* (2018.01)
*G06F 19/00* (2018.01)
*G06T 11/20* (2006.01)
*G06K 9/00* (2006.01)
*H04N 5/225* (2006.01)

(52) U.S. Cl.
CPC .......... *G06N 20/00* (2019.01); *G06T 7/0012* (2013.01); *G06T 7/70* (2017.01); *G06T 11/206* (2013.01); *G16H 50/30* (2018.01); *G06K 2209/05* (2013.01); *G06T 2207/10016* (2013.01); *G06T 2207/20072* (2013.01); *G06T 2207/20076* (2013.01); *G06T 2207/20081* (2013.01); *H04N 5/2252* (2013.01)

(58) Field of Classification Search
CPC ........ G06K 9/4604; G06T 2207/10028; G06T 2207/10032; G06T 2207/10044; G06T 2207/30184; G06T 7/0004; G06T 7/13; G06T 7/521; G06T 7/66; G06T 7/73; H04N 13/10; H04N 5/2251
See application file for complete search history.

(56) References Cited

U.S. PATENT DOCUMENTS

| | | | |
|---|---|---|---|
| 2009/0112541 A1 | 4/2009 | Anderson et al. | |
| 2012/0113209 A1 | 5/2012 | Ritchey et al. | |
| 2012/0139828 A1 | 6/2012 | Lok et al. | |
| 2012/0150333 A1* | 6/2012 | De Luca | G06K 9/00281 700/109 |
| 2012/0154582 A1 | 6/2012 | Johnson et al. | |
| 2012/0212582 A1 | 8/2012 | Deutsch | |
| 2012/0316497 A1* | 12/2012 | Deutsch | A61M 5/5086 604/111 |
| 2013/0113931 A1 | 5/2013 | Alper | |
| 2013/0122807 A1 | 5/2013 | Tenarvitz | |
| 2014/0328521 A1* | 11/2014 | Colangelo | H04L 67/18 382/118 |
| 2015/0199484 A1* | 7/2015 | Morris | G06F 19/3456 705/2 |

OTHER PUBLICATIONS

Curran, Padraig, et al. "VAMP—a vision based sensor network for health care hygiene," Conference Item, 2008.
J.P. Haas et al., "Measurement of compliance with hand hygiene," Journal of Hospital Infection, 2007.
T.G. Zimmerman, "Personal area network: Near-field intrabody communication," IBM Systems Journal, vol. 35, Nos. 3&4, 1996.
List of IBM Patents or Patent Applications Treated as Related dated Dec. 28, 2016, 2 pages.
List of IBM Patents or Patent Applications Treated as Related Dated Apr. 5, 2017, 2 pages.
Non Final Office Action for U.S. Appl. No. 15/392,599 dated Jun. 28, 2019 (23 pages).
Final Office Action for U.S. Appl. No. 15/392,599 dated Dec. 12, 2019 (24 pages).
List of IBM Patents or Patent Applications Treated as Related dated Apr. 4, 2017, 2 pages.

* cited by examiner

HEAD MOUNTED VIDEO AND TOUCH DETECTION FOR HEALTHCARE FACILITY HYGIENE

FIELD OF THE INVENTION

The invention disclosed broadly relates to the field of healthcare hygiene, and more particularly relates to the field of touch detection to prevent contamination and spread of bacteria.

BACKGROUND OF THE INVENTION

Infections are a large and growing problem in healthcare environments today. Many healthcare environments such as hospitals are plagued by antibiotic-resistant bacteria. The demands on healthcare workers include constant vigilance for contaminated surfaces and opportunities for transmission, as well as costly management of patients who are carriers. Healthcare workers themselves can become colonized by these strains of microorganisms, and face job loss as a result.

Germs can live on surfaces for a long time. Some gram-positive bacteria can survive for months on dry surfaces. Blood-borne pathogens, such as HBV and HIV, can live for days outside of the body. Some of the most common nosocomial pathogens may well survive or persist on surfaces for months and can thereby be a continuous source of transmission if no regular preventive surface disinfection is performed.

As workloads increase with cost-cutting measures in the healthcare space, the ability of workers to manage the cognitive load of attending to and tracking contact with all surfaces in order to maintain proper hygiene and prevent the spread of drug resistant bacteria is therefore challenged. Hand hygiene is a simple solution and studies show that proper hand hygiene is a huge factor in thwarting the spread of germs. Even though hand hygiene is well known as an important step in healthcare vigilance, and reminders are ubiquitous in hospital settings, hospital workers are not always aware of everything they touch. Also, the quality of hand washing is a factor. Plus, compliance is a problem because hand-washing is a self-regulated act.

Typically, all of the control mechanisms in facilities today depend on the vigilance of healthcare workers, and the existing solutions in practice today are therefore extremely vulnerable. If only one worker fails to execute proper hygiene the entire system is threatened. There is a need for a system and method to overcome the above-stated shortcomings of the known art.

SUMMARY

Briefly, according to an embodiment of the present disclosure, a method tracks touches in order to analyze paths of transmission and contamination for the purpose of eliminating and containing transmission of colonizing, drug-resistant pathogens. The method can be implemented in a healthcare setting, in a school, subway, or in any environment where public safety is a major concern. In this method, touches are identified and tracked with the use of recording devices. Each touch is logged and a touch graph is generated to identify transmission paths.

According to another embodiment of the present disclosure, a touch detection system tracks touches in a healthcare environment in order to identify transmission paths of deleterious entities. The system includes various components such as forward-facing recording devices, PANs, and processing components for performing analysis and recommending mitigating actions. The deleterious entities can be any of: microorganisms, toxins, anthrax spores, ricin, or the like. The recording devices and PANs not only record the touches, but are used to increase the confidence level of object identification, as well as providing data about the nature of the risk involved.

BRIEF DESCRIPTION OF THE SEVERAL VIEWS OF THE DRAWINGS

To describe the foregoing and other exemplary purposes, aspects, and advantages, we use the following detailed description of an exemplary embodiment of the disclosure with reference to the drawings, in which.

Figure 1B:
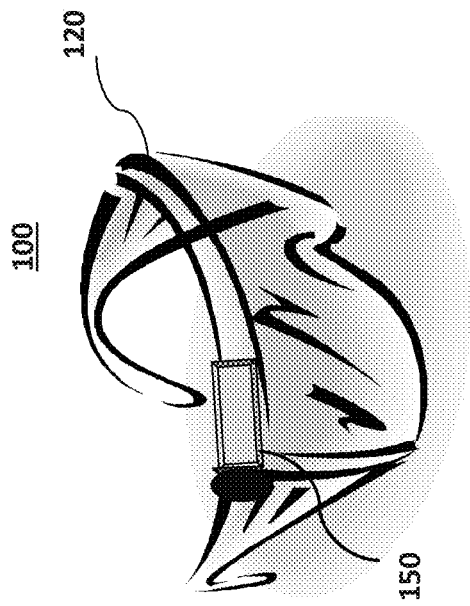
FIG. 1B is a close-up view of a head-mounted display, according to the known art.

While embodiments of the disclosure, as claimed, can be modified into alternative forms, specific embodiments thereof are shown by way of example in the drawings and will herein be described in detail. It should be understood, however, that the drawings and detailed description thereto are not intended to limit the disclosure to the particular form disclosed, but on the contrary, the intention is to cover all modifications, equivalents and alternatives falling within the scope of the present disclosure.

DETAILED DESCRIPTION

Before describing in detail embodiments that are in accordance with the present disclosure, it should be observed that the embodiments reside primarily in combinations of method steps and system components related to systems and methods for placing computation inside a communication network. Accordingly, the system components and method steps have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Thus, it will be appreciated that for simplicity and clarity of illustration, common and well-understood elements that are useful or necessary in a commercially feasible embodiment may not be depicted in order to facilitate a less obstructed view of these various embodiments.

Definitions of terms used throughout this disclosure:

augmented reality coloration—a technology that assigns different colors to different objects or views of objects; used with augmented reality devices such as head-mounted displays deleterious entity—a chemical, physical, or biological entity that can cause harm gram-positive bacteria—multi-drug resistant bacteria that are stained dark blue by gram staining HBV—Hepatitis B virus HIV—Human Immunodeficiency Virus HMD—head-mounted display—an augmented reality hands-free wearable computing device LCD (liquid crystal display)—an electronic visual display LCoS (liquid crystal on silicon)—an electronic visual display using a liquid crystal layer on silicon MSRA—Methicillin-resistant *Staphylococcus aureus* causes infections that are tougher to treat than most staph infections because of its resistance to commonly-used antibioticsnosocomial infection—an infection originating in a hospital OLED (organic light-emitting diode)—a visual display medium pathogen—an infectious agent that can produce a disease PAN (personal area network)—near-field intra-body communication ricin—a deadly toxin that is the byproduct of making castor oil We describe a method, service, and system that tracks touches in a healthcare environment in order to analyze paths of transmission and contamination for the purpose of automatically limiting transmission of colonizing, drug-resistant pathogens. By automatically comparing paths of transmission with real-world detection of microorganisms on surfaces of objects and the skin of workers, a means is disclosed to automatically identify problem areas that can be targeted for improved hygiene. To this end we combine: 1) head-mounted forward-facing video cameras (e.g. Google Glass™) used by healthcare workers such as doctors and nurses; 2) object recognition applied to the video stream, and 3) the automated creation and analysis of a contact graph. This approach is likely to save hospitals money in the long run due to reduced costs, reduced disease incidence, and reduced liability, to name a few. Just as important, many hospital workers will consider this as an aid in following correct procedures and also help create a healthier working environment for the workers themselves.

Currently, there is no known solution that makes use of these multi-disciplinary techniques in a healthcare environment as a service for the purpose of automatically limiting transmission of colonizing, drug-resistant bacteria. One with knowledge in the art will appreciate that the embodiments discussed herein, although focused on healthcare environments for discussion purposes only, can be implemented in other environments as well. For example, in this age of terrorism, the embodiments described herein can be advantageously implemented to thwart the transmission of toxins, ricin, anthrax spores, and the like in mass transit stations, airports, and other environments where the safety of the general population can be at risk.

Figure 1A:
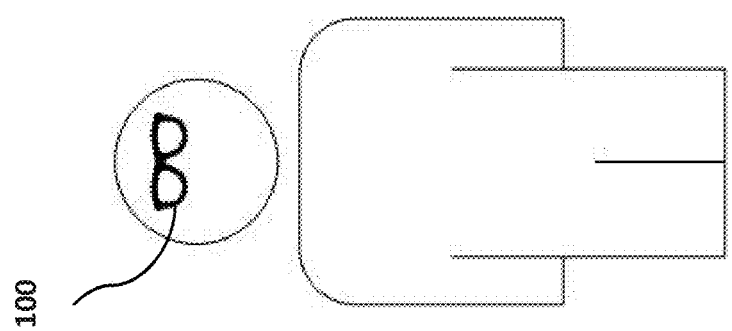
FIG. 1A is an exemplary depiction of a healthcare provider wearing a head-mounted display, according to the known art.

FIGS. 1A and 1B—Video Recording Device.

Referring now to FIG. 1A there is shown a depiction of a health-care provider wearing a head-mounted display (HMD) 100 with a built-in camera and touchpad, as is known in the art. HMDs are wearable intelligent devices, worn by the user like a pair of eyeglasses. They display information and interact with the Internet in a hands-free format, using natural language voice commands. FIG. 1B is a close-up image of the HMD 100 showing that a typical HMD 100 includes a casing 120 in the form of a headband, eyeglasses or goggles, as well as components 150 normally found in smart phones, such as a camera, a processor, a network interface, and a micro display.

Thanks to technological advances in computing and photographic devices, audio and video recording devices are getting smaller. In another embodiment of the present disclosure, the audio and video recording device is not a head mounted display, but is instead a small, forward-facing camera device worn on a lanyard or clothing of the healthcare worker. The camera device can even be coupled with the healthcare worker's ID card.

Figure 2:
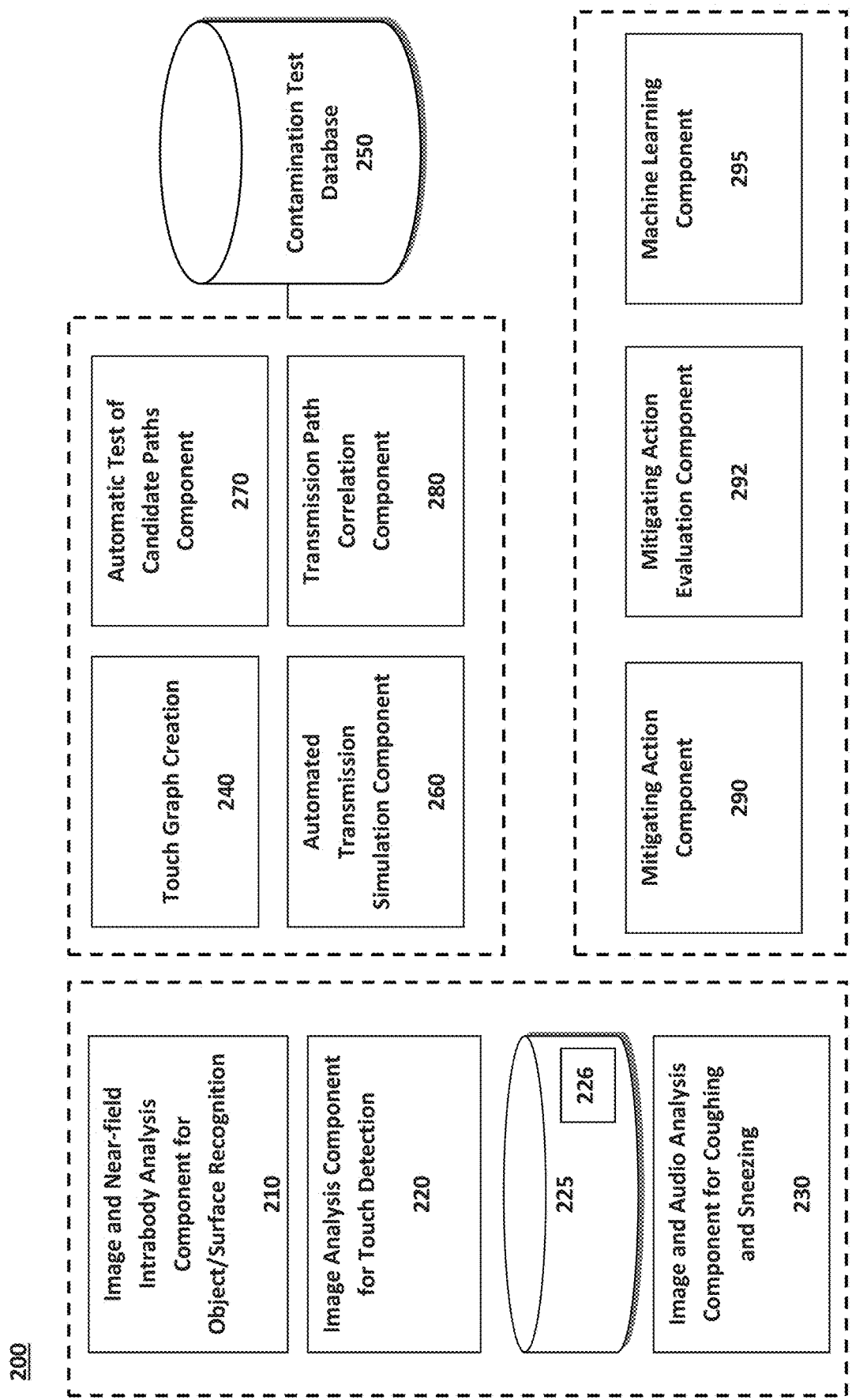
FIG. 2 is a simplified block diagram showing the components of the touch detection and analysis system, according to an embodiment of the present disclosure.

FIG. 2—Touch Detection and Analysis System.

Referring now to the drawings in general and to FIG. 2 in particular, we show additional components of the Touch Detection and Analysis System 200, according to an embodiment of the present disclosure. Although not all of the following components are required to operate the Touch Detection and Analysis System 200 together with the HMD 100, they are provided below for completeness so as to facilitate a working System 200.

PAN—Image and Near-field Intrabody Analysis Component for Object/Surface Recognition 210. In one embodiment, healthcare workers in a healthcare environment are assigned unique IDs and equipped with a recording device that records objects and patients in the worker's environment and catalogues these in a database shared among workers. Each object is assigned an object ID. Touchable surfaces are identified and each is assigned a surface ID. Each patient is also assigned a patient ID. As an example, nurse 0038, janitor 1032, and physician 0005 may or may not interact a number of times with heart monitor 0010, bed rail 1013, and sink handle 0105.

Figure 7:
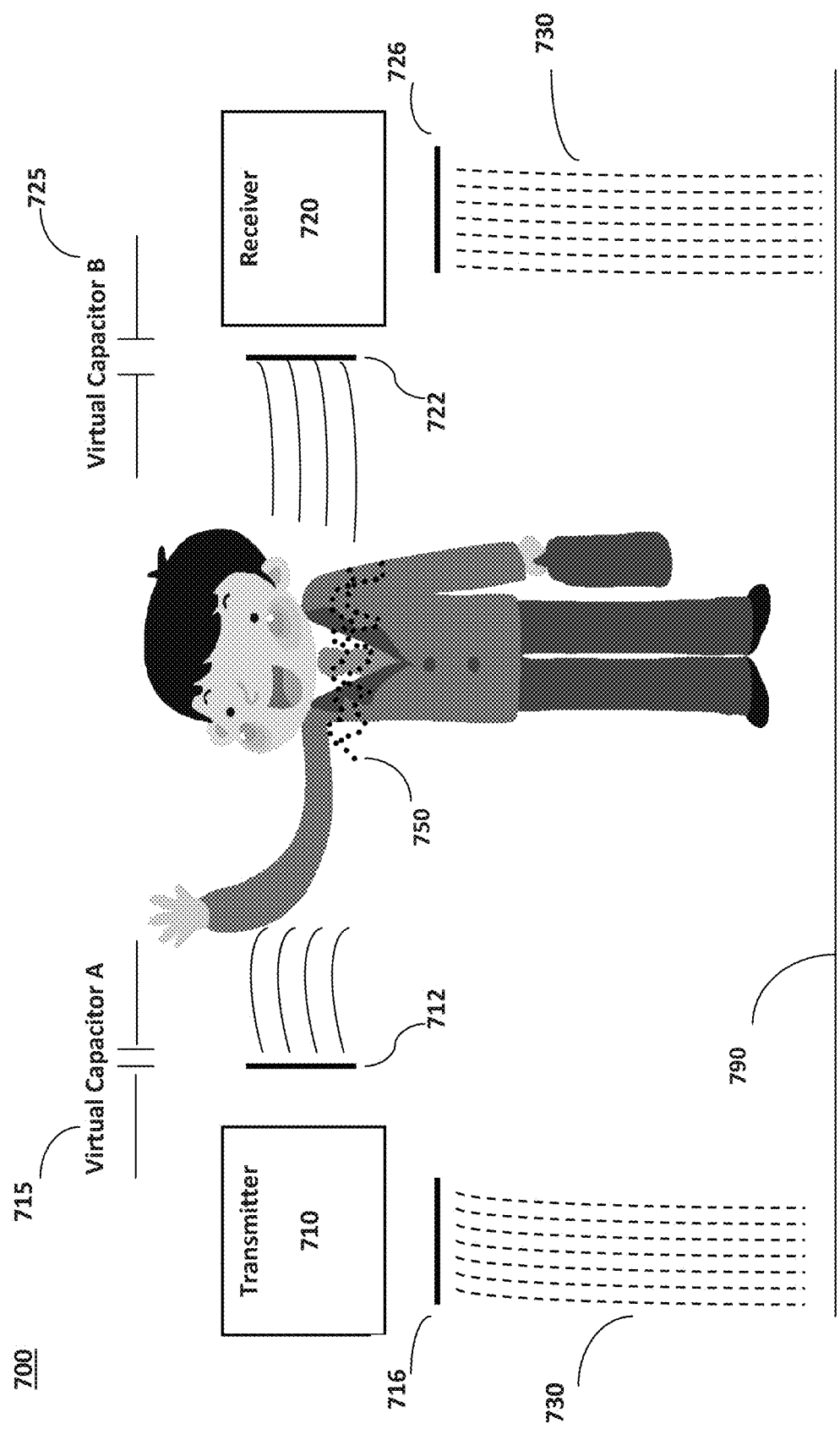
FIG. 7 is a simplified illustration of how a PAN works, according to the known art.

As a further example, "objects" may also include people who may touch surfaces, and the nature of this contact may be gleaned, in part, by both a video system and a PAN (Personal Area Network) system that uses near-field intra-body communication as is known in the art. Referring now to FIG. 7, a PAN 700 is a network consisting of electronic devices that are commonly found on or near a human body, such as cellular phones, personal digital assistants (PDAs), and the like. Normally these devices do not share information, but within a PAN, these electronic devices operate to exchange digital information using the human body's own electrical currents 750 as transmission paths. A PAN near-field intrabody communication system uses the human body as an electrical medium, capacitively coupling the picoamp currents 750 that naturally run through the human body. A PAN Transmitter 710 with a Transmitter Electrode 712 act as a capacitor (Virtual Capacitor A 715), capacitively coupling current 750 through the human body to a PAN Receiver 720. The Receiver Electrode 722, with the Receiver 720, act as a capacitor (Virtual Capacitor B 725).

Another Receiver Electrode 726 facing Ground 790 act as Capacitor C, while another Transmitter Electrode 716 facing Ground 790 acts as Capacitor D. Electric fields 730 are thus generated between the Ground 790 and the electrodes 726 and 716. The mechanics of a PAN near-field intrabody communication system are beyond the scope of this disclosure. More information can be found in "Personal Area Network: Near-field intrabody communication" by T. G. Zimmerman published in IBM Systems Journal, Vol. 35, Nos. 3&4, 1996, which is incorporated by reference herein in its entirety. An example of a near-field intrabody system in use today allows users to exchange electronic business cards by shaking hands.

In this disclosure, we use streaming video data from multiple devices such as HMDs 100 and stationary cameras. The video data is collected and stored from each device. Because of the extremely large volume of potential video data, intelligent compression and filters are applied to reduce inconsequential (low risk) segments. An example possible area for data reduction may involve a hospital staff person who is walking down a hallway where no contact is made either with surfaces or other persons in a defined radius R, for a time period T, with a given consideration of possible transmission characteristics (e.g. airborne pathogen transmission).

In addition, the streaming video data may be processed in real-time and stored with metadata to identify or indicate "persons" and "locations" in the current stream (with optional use of facial recognition technology to identify staff and/or non-staff persons). With the video data available in this manner, crime-scene like techniques can be used to identify and follow the web of potential pathogen transmission sources, points of contact, and routes. Using analytic methods known in the art, a well-defined action plan may optionally be rapidly assembled to combat or respond to the potential threat. Based on information available, the HMD may be able to warn the wearer of potential problems (i.e., infected surfaces).

Image Analysis Component for Touch Detection 220. Cameras record the positions of workers' hands in the environment. The camera can be part of a HMD 100. Touches with surfaces are recorded and identified, and the associated object ID retrieved from a database 225. Objects' surfaces and patients determined to have been touched are entered in a touch database 225 according to the time, worker ID, object/patient ID, and surface ID. Touch detection may be facilitated by various means including any of: image analysis, bar code analysis, RFID analysis, QR code analysis, contact sensors, and the like. Similarly, personal area networks (PAN) using near-field intrabody communication can be used to facilitate aspects of touch characterization. We make use of various means to collect real-time touch data, including both head mounted displays (HMDs) 100, such as Google Glass™, and PANs 700 to facilitate aspects of touch characterization and boost the confidence level C of object identification in a complex and dynamically changing environment.

Touch Database 225. A Touch Database 225 is used for logging each occurrence of a touch. Each touch is logged with at least a timestamp, worker ID, object/patient ID, and surface ID. The Touch Database 225 may be separate or incorporated into the database storing the IDs.

Image and Audio Analysis Component for Coughing and Sneezing 230. This component can be employed to aid in identifying problem regions in a healthcare setting, along with timing information related to the time of potential contamination. We take advantage of cough-detection and sneeze-detection methodologies that are known in the art, such as that described in U.S. Pat. No. 8,241,223, "Cough Detector," issued to iSonea Limited on Aug. 14, 2012. In one method of cough detection, an algorithm identifies loud sounds with a cough pattern to search for cough "candidates." In another method, a cough detector worn around the neck uses ultrasound to detect coughs.

Touch Graph Creation Component 240. Using the touch occurrences logged in the Touch Database 225, we formulate a graph representation of the touch occurrences (shown in FIG. 4). Healthcare environment workers 410, patients and visitors 420, and object surfaces 430 (such as hospital equipment and furnishings) are each assigned a node on the Graph 400, with touches 450 represented as edges in the graph representation. Edges are bidirectional to represent potential transmission 460 of microorganisms in either direction during contact.

Contamination Test Database 250. Based either on a random sampling technique, or on specific samples ordered by the outputs of analyses of likely transmission paths, tests for contamination of objects' surfaces, patients, and workers are entered into the Database 250 and associated with their corresponding IDs and graph nodes from the Touch Graph.

Automated Transmission Simulation Component 260. When contamination with a single strain of bacteria is detected in two or more nodes, all possible transmission paths are automatically calculated using the Touch Graph. Traversal of this graph is time-dependent, in that transmission must occur in temporal order across two or more identified touches. Each path is entered in a transmission path database.

Automatic Test of Candidate Paths Component 270. The most parsimonious (fewest nodes/touches) path is then optionally identified from the database as the primary hypothesis, and a test of this hypothesis is ordered, involving a directed sample of a non-tested node in the transmission path, if possible. If the test is negative, the second most parsimonious path is tested, and so on.

Transmission Path Correlation Component 280. Over time, multiple positively tested transmission paths in the environment will be identified and noted in the transmission path database. These are then reanalyzed for correlated nodes to determine which nodes show a systematic and temporally correlated high likelihood for a role in transmission. These suspected paths are then ranked based on mitigation benefit, M, which is equal to a function $f$ of the likelihood of the path playing a role in the transmission of pathogens, L, the expected impact of a mitigating action on reducing transmission, P, and any other costs, benefits, or risks associated with mitigation, C, i.e., $M=f(L,P,C)$.

Note that each visitor may also be optionally assigned a tracking number. This service may be used to indicate what not to touch due to possible contamination. This could be indicated by various means, in real-time, as confidence level about problematic locations, devices, vents, buttons, monitors, IV poles, door knobs, faucets, or other objects increases. One may optionally flag a person walking around as being problematic. Note that analytics may be provided to determine the probability of a contaminated path, based on anonymized data of the patient's records, healthcare provider contacts, visitor contacts, and path taken or to be taken.

Mitigating Action Component 290. Mitigating actions are optionally then taken, directed at nodes identified as having the highest mitigation benefit, M. These actions can include scheduled sterilization of surfaces, isolation of a patient, or targeted education of health care workers on proper hygiene. Over time, multiple, positively-tested transmission paths in the environment will be identified and noted in the transmission path database. These are then reanalyzed for correlated nodes to determine which nodes show a systematic and temporally correlated high likelihood for a role in transmission. These suspected paths are then ranked based on mitigation benefit, M, which is equal to a function $f$, of the likelihood of the path, L, the expected impact of a mitigating action on reducing transmission, P, and any other costs, benefits, or risks associated with mitigation, C, i.e., $M=f(L,P,C)$.

An additional mitigating action may optionally include advising health care workers on movement paths through the hospital for them, patients, and visitors so as to minimize risk of transmission. Not only does the service automatically indicate problem paths (e.g. paths that might be avoided or cleaned, or avoided until cleaned with an automatic trigger to cleaning staff), but the system may optionally can show paths that are likely to be good (with a confidence level). Of course, a "good" path might cross the threshold to "bad" after N people have traversed it, with N being a large number, and if the people traversing the path have touched objects with possible problems.

The head-mounted display 100 may optionally specify the nature of a problem that concerns a traversal path, a contaminated object, a person to avoid, a hallway to avoid, a hallway to use, an object to use, etc. For example, augmented reality coloration can suggest, with confidence level C, that a path, object, or person is associated with one or more microorganisms, toxin, sterility (or lack of sterility) level, and the like. For example, different colors can be applied to different objects in order to easily distinguish among types of objects. This kind of optional mitigating component may based on extending the use of the head mounted displays beyond collecting data on objects touched by health care workers. The service may also use the head mounted displays to also provide feedback to the health care workers on what not to touch. One intriguing aspect of the use of HMDs 100 is the means to integrate data from the forward facing camera based analysis of transmission with a real-time feedback from the HMD 100. For both visitors and health care workers this seems like a valuable addition to the invention Mitigation Action Evaluation Component 292. After a mitigating action is optionally taken, follow-up analyses of transmission paths may determine if a change in the transmission topology through the touch graph is realized by the action. If no change in transmission topology occurs, P is adjusted for those nodes previously mitigated, and a new mitigating action determination is ordered, based on the new findings.

Machine-Learning Component 295. Over time, the evaluation of mitigating actions may optimally be identified by machine learning. Machine learning can provide the indication that certain classes of candidate hypothetical transmission paths are unlikely, despite correlations in the touch graph. The graph can be updated (for example, even though it appeared that person 0001 was contaminated, later tests may reveal this to be inaccurate), but just as likely, this more directly changes the calculation of M, as indicated in the following sentences. Mitigating actions are optionally then taken, directed at nodes identified as having the highest mitigation benefit, M. These may be due to the identity of the node, or other contextual inputs to the machine learning component. These determinations are then fed back into the calculation of the L and/or P for these nodes, the tough graph is updated, shaping future calculations of M. Analytics may be provided to determine the probability of a contaminated path, based on anonymized data of the patient's record, healthcare provider/visitor contact and path to be taken.

Head-mounted forward-facing video cameras are coupled with the Image and Near-field Intrabody Analysis Component for Object/Surface Recognition 210. These HMDs 100 come in many forms and form factors and the present embodiments cover a range of such wearable devices that may include one or two small displays with lenses, with semi-transparent mirrors embedded in a helmet, eye-glasses, visors, CRTs, LCDs, liquid-crystal on silicon (LCoS), OLED, "curved Mirror" HMDs, and "waveguide" HMDs, to name a few. Advanced head-mounted displays, including displays that resemble glasses such as Google Glass™, are becoming more popular.

Figure 4:
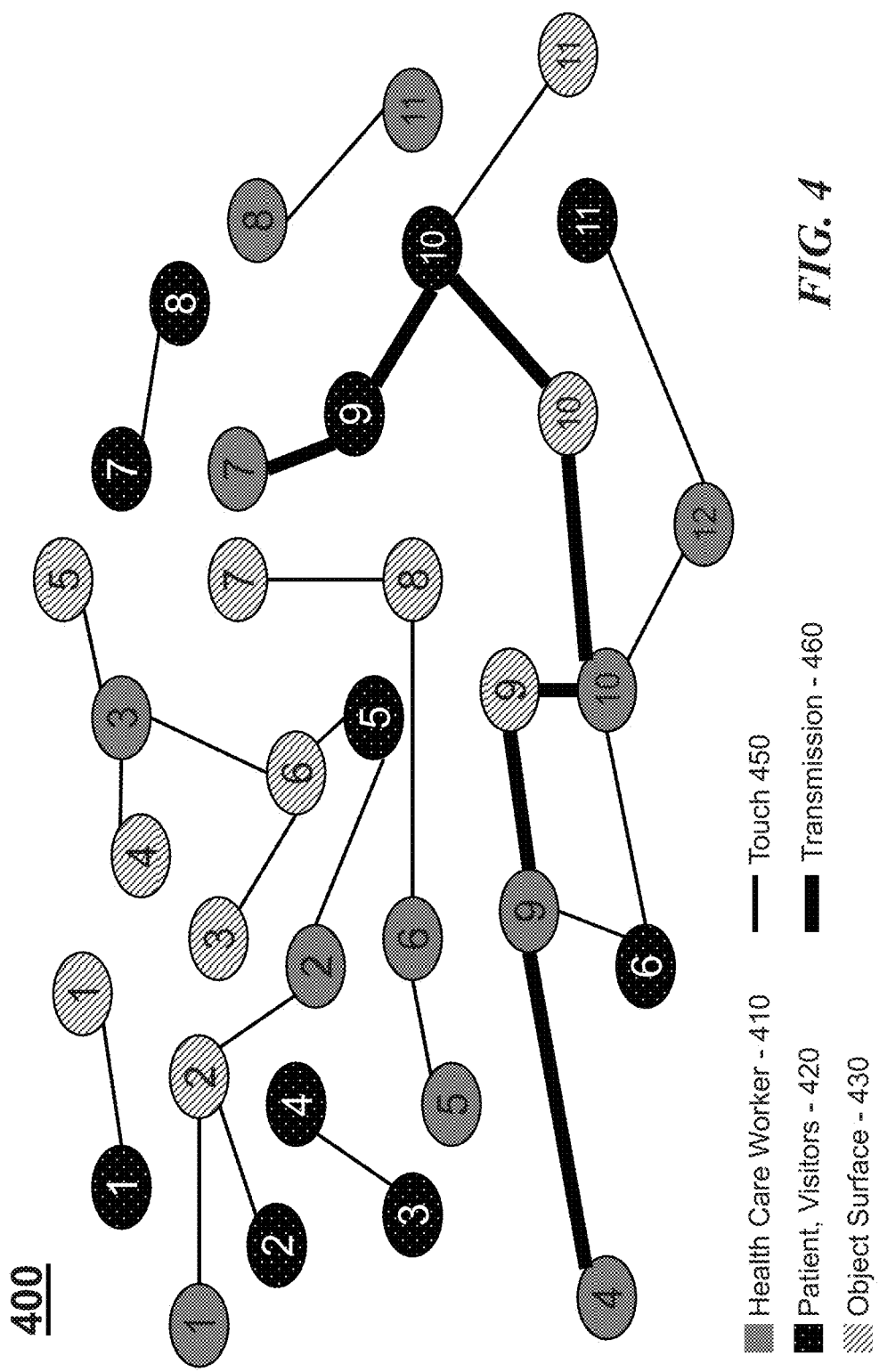
FIG. 4 is an exemplary illustration of a touch graph, according to an embodiment of the present disclosure.

FIG. 4—Transmission Graph. Referring now to FIG. 4, we provide an exemplary Transmission Graph 400. The Transmission Graph 400 includes nodes representing workers 410, patients and visitors 420, and touched objects 430. The touches among the nodes are the edges 450 of the graph. The transmission paths 460 are the set of connected nodes that provide the highest probability of contamination, shown here as a bold line. The Transmission Graph 400 provides a good visual indicator of those paths which are likely to be transmission paths for pathogens (candidate transmission paths 460) Likewise, the Transmission Graph 400 provides a good visual indicator of paths that are not problematic.

Service. The touch detection and analysis method according to this disclosure can be provided as a service for a fee. The service presented here has an initial up-front cost, however it is likely to save hospitals money in the long run due to reduced costs, disease incidence, liability, and other factors, while aiding hospital workers. The service disclosed herein employs several components that automatically implement the touch-detection and touch-graph analysis in order to identify candidate paths for transmission of microorganisms, and correlates and tests these candidate paths against observed paths of spread of contamination in the healthcare setting, or in any setting where the health and welfare of a large population of people is at risk.

FIG. 3—Flowchart.

Figure 3:
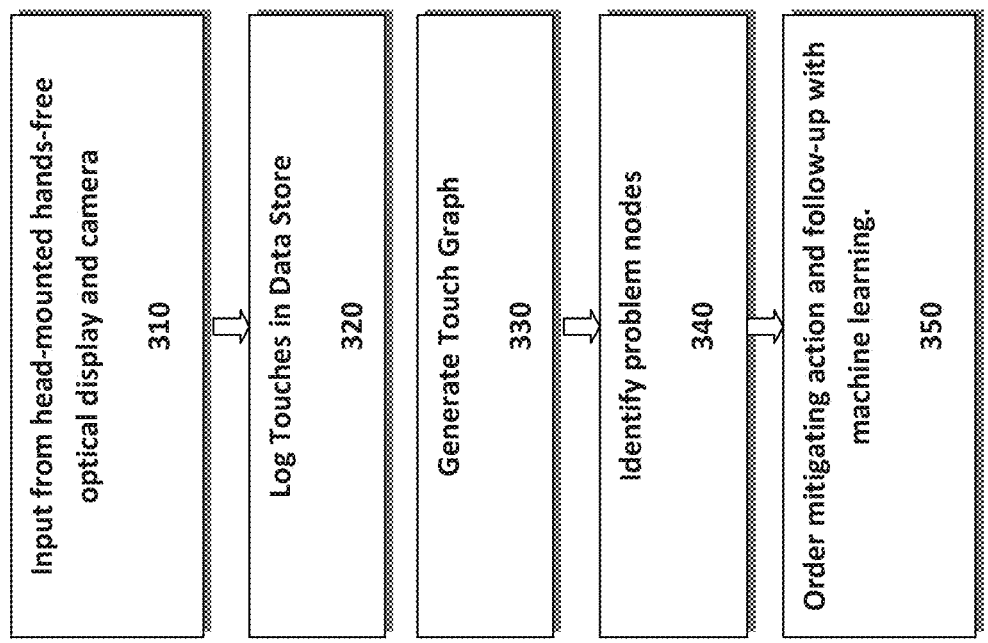
FIG. 3 is a high-level flowchart of the touch detection and analysis method, according to an embodiment of the present disclosure.

Referring now to FIG. 3 we show a high-level flowchart of a method for touch detection and analysis, according to one embodiment of the present disclosure. In step 310, we employ head mounted, hands-free optical displays outfitted with cameras, such as Google Glass™, to identify and record touches. By using these devices, we facilitate and increase the confidence of real-time touch data collection. In step 320, we log each recorded touch in a data store 225, noting the identifying information for each touch.

From the touch logs 226, we generate the Transmission Graph 400 to track pathogen transmission in step 330. The nodes in the Graph 400 represent hospital workers, patients, visitors, and touched objects, among other points of possible contact. In step 340 we identify any "problem nodes" and perform an automatic calculation of the impact of a mitigating action, with the automatic evaluation of likelihood of transmission based on automatically ordered hypothesis testing. We define "problem nodes" as those nodes that can be targeted for improved hygiene. Problem nodes are nodes that have a potential for being associated with a deleterious event such as pathogen or other harmful transmission. More particularly, these may be nodes with a preponderance of evidence pointing to involvement in one or multiple transmissions, such as a nurse who doesn't practice good hand washing.

In order to identify the problem nodes, we perform a sampling of surfaces, patients, and workers for contamination. The sampling can be performed in an automated fashion, such as through the use of many approaches known in the related art to detect microorganisms, which may be implemented by ambient devices. Some examples of these approaches are:

a) The use of detection devices ("polymers that fluoresce in the presence of bacteria, paving the way for the rapid detection and assessment of wound infection using ultraviolet light.")

b) Laser Nanosensors that detect Bacteria c) other approaches that may be deployed in an automated fashion use drones, robots, sensors, and devices on surfaces. One such approach is described in Patent WO 2013057731 "Methods of detecting the presence of microorganisms in a sample," by D.I.R. Technologies.

In step 350 the system automatically directs an appropriate mitigating action with follow-up analysis of effects on future transmission, as well as machine learning association of context with the action, for future refinement to the expected impact of mitigation. As previously stated, mitigating actions can include: advising health care workers on movement paths of pathogens; scheduled sterilization of surfaces; isolation; and targeted education of health care workers.

Figure 6:
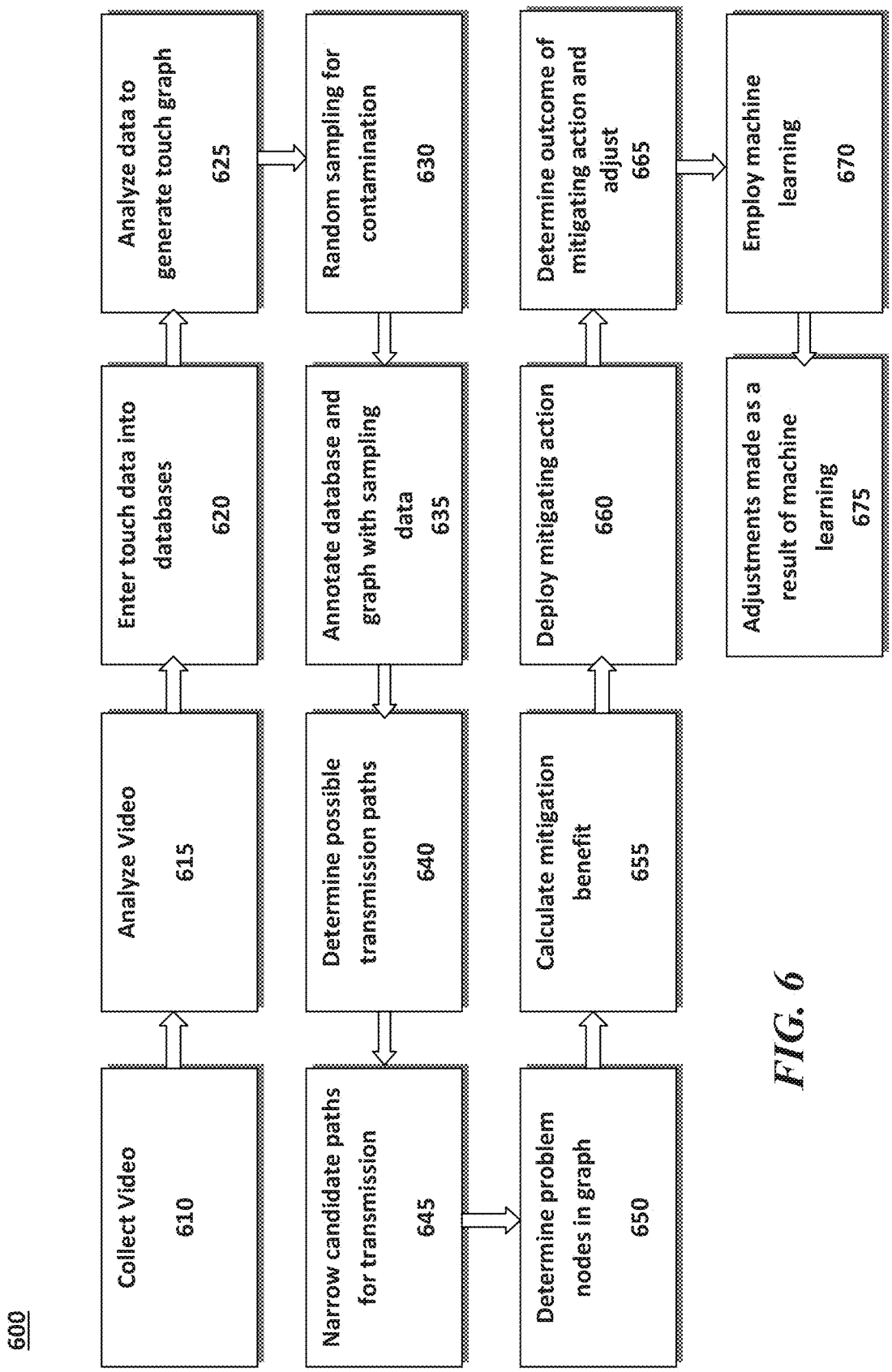
FIG. 6 is a lower-level flowchart of the touch detection and analysis method, according to an embodiment of the present disclosure.

Referring now to FIG. 6, we show a lower-level flowchart 600 of the touch detection and analysis method, according to an embodiment of the present disclosure. In step 610, we collect video and/or audio data of interactions among healthcare workers, patients and objects. We can employ forward facing head mounted cameras (HMDS) worn by health care workers. In step 615 we analyze the video for object surface recognition, surface touches, and patient touches by workers. The analysis can be performed by the HMD itself.

In step 620 all objects, surfaces, patients, workers, touches, and time of touches are automatically entered into touch logs 226, once they are identified. In step 625 the touch log data is analyzed to generate a Transmission Graph 400 wherein nodes correspond to object surfaces, patients, and workers, and touches/touch times correspond to edges 450 in the Transmission Graph 400.

In step 630 surfaces, patients, and workers can be sampled to test for contamination by identifiable strains of microorganism. The sampling can be performed randomly, at periodic intervals, or a targeted sampling can be performed in response to a specific indication of contagion. For example, if a case of MRSA is discovered on the fourth floor of a hospital, then a targeted sampling of all workers, patients, and objects on the fourth floor could be ordered.

In step 635 after we receive the results of the sampling, we annotate the database 225 and Transmission Graph 400 with contamination information. In step 640, for any two or more contaminated nodes, we determine all possible temporally ordered paths of transmission 460 between nodes and enter these paths 460 in the database 225. In step 645, we deploy tests to narrow candidate paths for transmission 460. As just one example, the tests mentioned above that concern automated sampling by drones or robots can be used to boost the accuracy and confidence level of possible contaminants. The HMDs can be employed to boost confidence levels as well. For example, nearby regions or the same regions may be retested, which may be useful in an environment that is constantly changing and for which transmission paths may be changing.

In step 650, we correlate candidate paths to determine problem nodes in the Transmission Graph 400. In step 655, we calculate a mitigation benefit M, as a function of a likelihood of the candidate path L being the transmission path 460, the expected impact from a mitigating action directed at reducing transmission P, and any other costs, benefits, or risks associated with the mitigation C. The formula is: $M=f(L,P,C)$. The suspected, or candidate, paths, are then ranked based on the calculated mitigation benefit, M. Paths may be analyzed and re-analyzed for correlated nodes to determine which nodes show a systematic and temporally correlated high likelihood L for a role in transmission.

In step 660, we deploy at least one mitigating action against nodes with the highest M values. Possible mitigating actions can be: a) cover a surface with antimicrobial film; b) schedule regular sterilization of equipment; c) ask visitors to don face masks before entering a patient's room; and d) use a germ-detecting UV (ultraviolet) light. In step 665, we analyze subsequent candidate transmission topology to determine if the mitigating action has had an effect. Then, we adjust expected future impacts of mitigating actions, M, accordingly. In step 670, we associate other contextual cues retrospectively with expected impacts of future mitigating actions M using machine learning. In step 675, we adjust the likelihood of transmission L through the nodes, and/or expected future impacts of mitigating actions, P, according to learned contexts.

Benefits and Advantages of the Disclosure.

The current disclosure has several advantages over known solutions for managing transmission of microorganisms in a healthcare environment, such as:

1. the coordinated use of multi-disciplinary technology such as head-mounted forward-facing cameras and sneeze detectors to collect real-time touch data;

2. creation of transmission graphs with automatic evaluation of likelihood, based on automatically ordered hypothesis testing;

3. identification of problem nodes and automatic calculation of the impact of a mitigating action; and 4. automatic ordering of mitigating action with follow up analysis of effects on future transmission, as well as machine learning association of context with the action, for future refinement to the expected impact of mitigation.

FIG. 5—Hardware.

Figure 5:
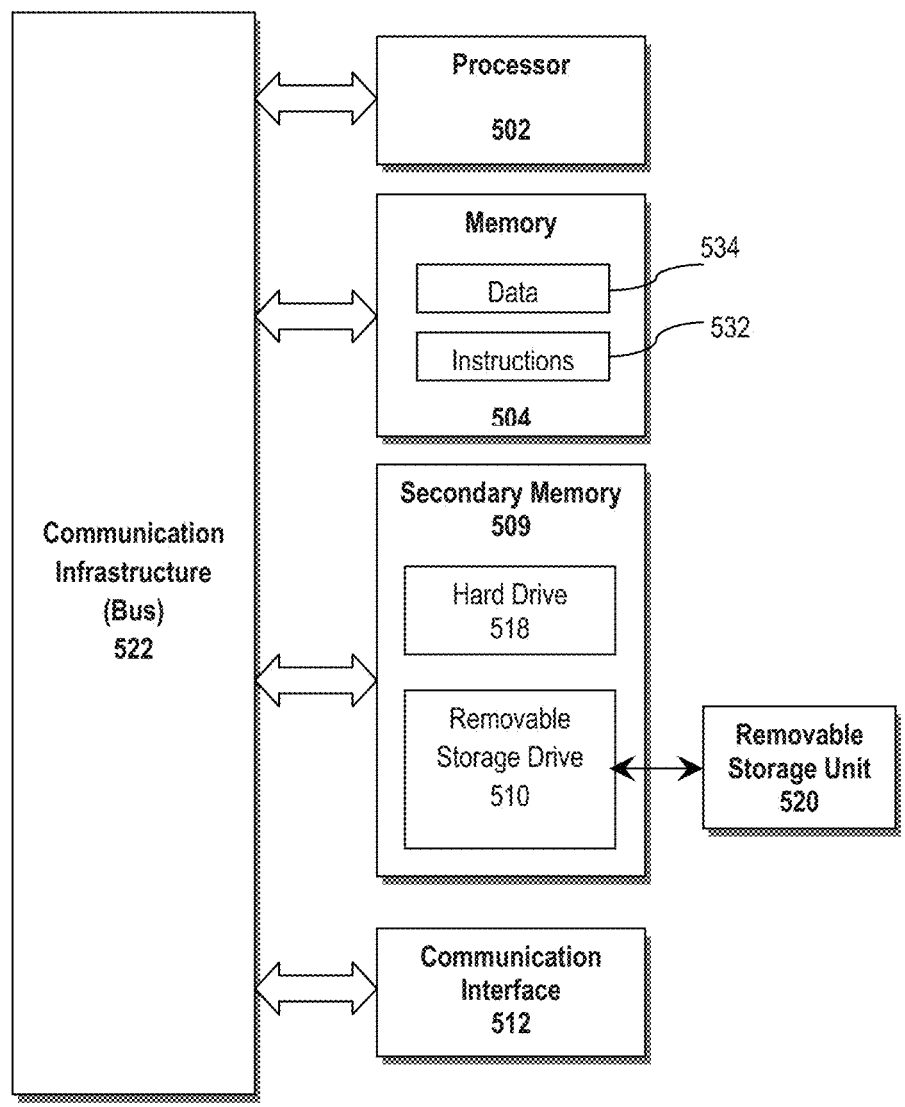
FIG. 5 is a high level block diagram showing an information processing system configured to operate according to an embodiment of the present disclosure.

Referring now to FIG. 5, there is provided a simplified pictorial illustration of the components of an information processing system 500 for touch detection and analysis in which embodiments of the present disclosure may be implemented. For purposes of this disclosure, computer system 500 may represent any type of computer, information processing system or other programmable electronic device, including a client computer, a server computer, a portable computer, an embedded controller, a personal digital assistant, Cloud computing, Internet TV, and so on. The computer system 500 is a networked computing device in communication with other computing devices such as the HMDs (not shown) via a network. As will be appreciated by those of ordinary skill in the art, the network may be embodied using conventional networking technologies and may include one or more of the following: local area networks, wide area networks, intranets, public Internet and the like.

Throughout the description herein, an embodiment of the disclosure is illustrated with aspects of the disclosure embodied solely on computer system 500. As will be appreciated by those of ordinary skill in the art, aspects of the invention may be distributed amongst one or more networked computing devices which interact with computer system 500 via one or more data networks such as, for example, network 510. However, for ease of understanding, aspects of the invention have been embodied in a single computing device—computer system 500.

Computer system 500 includes inter alia, processing device 502 which communicates with an input/output subsystem 506, memory 504, storage 510 and network 510. The processor device 502 is operably coupled with a communication infrastructure 522 (e.g., a communications bus, crossover bar, or network). The processor device 502 may be a general or special purpose microprocessor operating under control of computer program instructions 532 executed from memory 504 on program data 534. The processor 502 may include a number of special purpose sub-processors such as a comparator engine, each sub-processor for executing particular portions of the computer program instructions. Each sub-processor may be a separate circuit able to operate substantially in parallel with the other sub-processors.

Some or all of the sub-processors may be implemented as computer program processes (software) tangibly stored in a memory that perform their respective functions when executed. These may share an instruction processor, such as a general purpose integrated circuit microprocessor, or each sub-processor may have its own processor for executing instructions. Alternatively, some or all of the sub-processors may be implemented in an ASIC. RAM may be embodied in one or more memory chips.

The memory 504 may be partitioned or otherwise mapped to reflect the boundaries of the various memory subcomponents. Memory 504 may include both volatile and persistent memory for the storage of: operational instructions 532 for execution by CPU 502, data registers, application storage and the like. Memory 504 preferably includes a combination of random access memory (RAM), read only memory (ROM) and persistent memory such as that provided by a hard disk drive 518. The computer instructions/applications that are stored in memory 504 are executed by processor 502. The computer instructions/applications 532 and program data 534 can also be stored in hard disk drive 518 for execution by processor device 502. Those skilled in the art will appreciate that the functionality implemented within the blocks illustrated in the diagram may be implemented as separate components or the functionality of several or all of the blocks may be implemented within a single component.

The computer system 500 may also include a communications interface 412. Communications interface 512 allows software and data to be transferred between the computer system and external devices. Examples of communications interface 512 may include a modem, a network interface (such as an Ethernet card), a communications port, a PCM-CIA slot and card, etc. Software and data transferred via communications interface 512 are in the form of signals which may be, for example, electronic, electromagnetic, optical, or other signals capable of being received by communications interface 512.

Computer Program Product.

Also with reference to FIG. 5, embodiments of the present disclosure may be a system, a method, and/or a computer program product. The computer program product may include a computer readable storage medium 520 (or media) having computer readable program instructions thereon for causing a processor to carry out aspects of the present disclosure.

The computer readable storage medium 520 can be a tangible device that can retain and store instructions for use by an instruction execution device. The computer readable storage medium 520 may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium 520, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium 520 or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions 532 for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language, and conventional procedural programming languages, such as the "C" programming language or similar programming languages. The computer readable program instructions 532 may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions 532 may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium 520 having instructions stored therein comprises an article of manufacture including instructions which implement aspects of the function/act specified in the flowchart and/or block diagram block or blocks.

The computer readable program instructions 532 may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions 532 for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Therefore, while there have been described embodiments of the present disclosure, it will understood by those skilled in the art that other modifications can be made within the spirit of the disclosure. The above descriptions of embodiments are not intended to be exhaustive or limiting in scope. The embodiments, as described, were chosen in order to explain the principles of the disclosure, show its practical application, and enable those with ordinary skill in the art to understand how to make and use the disclosure. It should be understood that this disclosure is not limited to the embodiments described above, but rather should be interpreted within the full meaning and scope of the appended claims.

What is claimed is:

1. A method for touch detection and analysis, comprising using a processor device, performing steps of:
   generating an indication that a touch has occurred with an object recognition device analyzing images captured with a video camera;
   generating a transmission graph from touches to identify deleterious entity transmission paths associated with a location, said transmission graph comprising:
      a plurality of nodes representing people, objects, and surfaces involved in touch occurrences throughout the location; and
      edges between the nodes representing interrelationships of the nodes;
   analyzing the transmission graph in real-time to identify one or more candidate transmission paths;
   calculating, for each of the one or more candidate transmission paths, at least one mitigation benefit for performing a mitigating action proposed to prevent deleterious entity transmissions, including deriving the at least one mitigation benefit based on a likelihood function of a likelihood of the candidate transmission path playing a role in deleterious entity transmission, an expected impact of the mitigating action on reducing transmission, and costs, benefits and risks associated with the mitigating action; and
   triggering mitigation of at least one problem node identified in the transmission graph based on the at least one mitigation benefit.

2. The method of claim 1, further comprising using the processor device to perform evaluating effects of the mitigating action.

3. The method of claim 2, further comprising using the processor device to perform updating the transmission graph according to the evaluation of the effects of the mitigating action.

4. The method of claim 1, wherein analyzing the transmission graph further comprises performing a sampling of at least one of: a plurality of identified persons, a plurality of identified objects, and a plurality of identified surfaces represented in the transmission graph to test for contamination.

5. The method of claim 4, further comprising:
   receiving results of the sampling; and
   using the results to automatically generate the one or more candidate transmission paths.

6. The method of claim 1 further comprising ranking the at least one mitigation benefit, wherein the mitigation of the at least one problem node is triggered based on the ranking.

7. The method of claim 1, wherein capturing images with a video camera comprises receiving touch identification from a touch identification system comprising at least one of: a head-mounted display camera and an intrabody near-field communication network.

8. The method of claim 1, further comprising:
   automatically analyzing the data to identify the touch; and
   logging the touch occurrence in a touch store.

9. An information processing system for touch detection and analysis comprising:
   a processor device; and
   a memory operably coupled with the processor device, said memory comprising computer-executable instructions for performing:
      generating an indication that a touch has occurred with an object recognition device analyzing images captured with a video camera;
      generating a transmission graph from touches to identify deleterious entity transmission paths associated with a location, said transmission graph comprising:
         a plurality of nodes representing people, objects, and surfaces involved in touch occurrences throughout the location; and
         edges between the nodes representing interrelationships of the nodes;
      analyzing the transmission graph in real-time to identify candidate transmission paths;
      calculating, for each of the one or more candidate transmission paths, at least one mitigation benefit for performing a mitigating action proposed to prevent deleterious entity transmissions, including deriving the at least one mitigation benefit based on a likelihood function of a likelihood of the candidate transmission path playing a role in deleterious entity transmission, an expected impact of the mitigating action on reducing transmission, and costs, benefits and risks associated with the mitigating action; and triggering mitigation of at least one problem node identified in the transmission graph based on the at least one mitigation benefit.

10. The information processing system of claim 9, wherein the computer-executable instructions further comprise ranking the at least one mitigation benefit, wherein the mitigation of the at least one problem node is triggered based on the ranking.

11. The information processing system of claim 9, wherein the video camera is a touch identification system comprising at least one of: a head-mounted display and an intrabody near-field communication network; and wherein the images are a combination of video data and audio data.

12. The information processing system of claim 11, wherein the video camera is to increase confidence levels in the identification of the one or more candidate transmission paths.

13. The information processing system of claim 9, wherein the setting comprises a healthcare facility.

14. The information processing system of claim 9, wherein the memory further comprises computer-executable instructions for performing:

automatically analyzing the data to identify the touch; and logging the touch occurrence in a touch store.

15. A method for automatically identifying transmission paths of deleterious entities in a health care environment, said method comprising:

using a processor device coupled with a recording device, performing:

generating an indication that a touch has occurred with an object recognition device analyzing images captured with a video camera;

identifying touched objects, surfaces, and people associated with a location from analysis of the images;

generating a transmission graph with nodes representing the objects, surfaces, and people throughout the location, and edges between the nodes representing interrelationships of the nodes;

analyzing the transmission graph in real-time to identify candidate transmission paths;

calculating, for each of the one or more candidate transmission paths, at least one mitigation benefit for performing a mitigating action proposed to prevent deleterious entity transmissions, including deriving the at least one mitigation benefit based on a likelihood function of a likelihood of the candidate transmission path playing a role in deleterious entity transmission, an expected impact of the mitigating action on reducing transmission, and costs, benefits and risks associated with the mitigating action; and triggering mitigation of at least one problem node identified in the transmission graph based on the at least one mitigation benefit.

16. The method of claim 15, further comprising ranking the at least one mitigation benefit, wherein the mitigation of the at least one problem node is triggered based on the ranking.

17. The method of claim 15, further comprising performing an automatic evaluation of mitigation impact to modify future impact predictions.

* * * * *